United States Patent

Sillekens

[11] Patent Number: 5,876,937
[45] Date of Patent: Mar. 2, 1999

[54] METHOD FOR DETERMINING THE INTEGRITY OF NUCLEIC ACID

[75] Inventor: Peter Theodorus Gerardus Sillekens, Gemonde, Netherlands

[73] Assignee: Akzo Nobel N.V., Arnhem, Netherlands

[21] Appl. No.: 793,717

[22] PCT Filed: Jul. 1, 1996

[86] PCT No.: PCT/EP96/02996

§ 371 Date: Jun. 6, 1997

§ 102(e) Date: Jun. 6, 1997

[87] PCT Pub. No.: WO97/03200

PCT Pub. Date: Jan. 30, 1997

[30] Foreign Application Priority Data

Jul. 3, 1995 [EP] European Pat. Off. .............. 95201805

[51] Int. Cl.⁶ .............................. C12Q 1/68; C07H 21/04; C12P 19/34
[52] U.S. Cl. ......................... 435/6; 435/91.2; 435/91.21; 435/91.5; 435/91.51; 536/24.31; 536/24.33; 935/8; 935/78
[58] Field of Search ................................. 435/6, 9.2, 91.5, 435/91.21, 91.51; 536/24.33, 24.31; 935/8, 78

[56] References Cited

FOREIGN PATENT DOCUMENTS 0313156   4/1989   European Pat. Off. .
4416446   11/1994   Germany .

OTHER PUBLICATIONS

C. Pannetier et al., *Nucleic Acid Research*, 21:3:577–583, Feb. 11, 1993.
K.E. Noonan et al., *PNAS*, 87:18:7160–7164, Sep. 1990.
J. Chelly et al., *Nature*, 333:858–860, Jun. 30, 1988.
J.W. Brown et al., *Plant Journal*, 4:5:883–885, Nov. 1993.
R.L.H. Nelissen et al., *Gene*, 102:2:189–196, 1991.
K.B. Mullis et al., *The Polymerase Chain Reaction*, 1994, Chapter 6, pp. 72–73.

*Primary Examiner*—Carla J. Myers
*Attorney, Agent, or Firm*—Mary E. Gormley

[57] ABSTRACT

The subject invention is directed to a method for determining the integrity of nucleic acid isolated from a specimen of eukaryotic origin comprising subjecting the specimen to nucleic acid isolation followed by amplification using a pair of oligonucleotide primers in a manner known per se, said primers being capable of amplifying nucleic acid specific for RNA encoding a product of a housekeeping gene, said RNA being low abundance RNA, said gene being present in all cell types of a eukaryotic species, and said method further comprising determining whether amplification of the nucleic acid specific for the RNA has occurred. In particular, the method comprises amplifying mRNA. Optionally, the method can also comprise quantifying the amplification product. As this method is of particular relevance for diagnosis of diseases in humans, the eukaryotic species is preferably a human being.

13 Claims, 8 Drawing Sheets

```
CGTATCCAGTATGCCAAGACCGACTCAGATATCATTGCCAAGATGAAAGGCACCTTCGTGGAGCGGGACCGCAAGCG.......
          5'-CAGTATGCCAAGACCGACTCAGA-3'.......
                      snRNP-U1A2.2

GGAGAAGAGGAAGCCCAAGAGACCAGGAGACCCCGGCCACCAAGAAGGCTGTGCAAGGGGGGAGCCACCCCCGTG
5'-AGAAGAGGAAGCCCAAGAGCCA-3'  snRNP-U1A HRP1
                          EXON3 | EXON4
GTGGGGGGCTGTCCAGGGGCCTGTCCCG | GGCATGCCGCCGATGACTCAGGCGCCCCGCATTATGCACCACATGCCGGG
                                                                          3'-AATACGTGGTGTACGGCCC.......
                                              5'-GCATGCCGCCGATGACTCA-3'  snRNP-U1A RA1

CCAGCCGCCCTACATGCCGCCCCCCCTGGTATGATCCCCCGC.......                                snR
Ggagaggatatcactcagcataatcttaa-5'

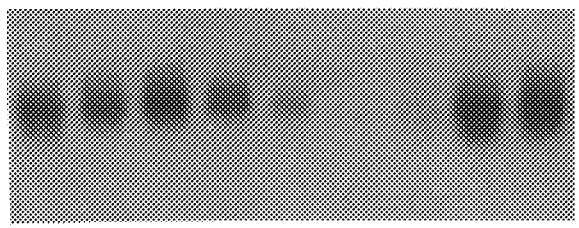
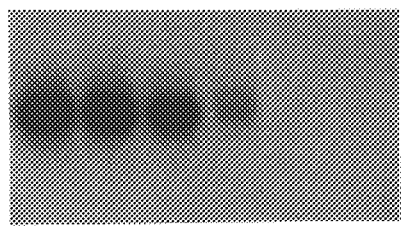
FIG. 3A
FIG. 3B

PATIENTS

CONTROLS

METHOD FOR DETERMINING THE INTEGRITY OF NUCLEIC ACID

DESCRIPTION

The subject invention lies in the field of nucleic acid and is directed in particular at methods wherein nucleic acid is isolated from cells, in particular eukaryotic cells. As any person skilled in the art will acknowledge methods using nucleic acid are frequently time consuming and uncertain in outcome due to the instability of nucleic acid material. In particular this is the case for RNA which is extremely sensitive to degradation. In particular in tests which are directed at determining whether a specific nucleic acid sequence is present in a sample it is important to be able to determine whether the sequence to be detected was in fact absent in the original sample or has been degraded during the method steps the sample has been subjected to, thereby leading to a false negative result. In particular in clinical diagnoses on the nucleic acid level a quality control of the nucleic acid that is extracted from such a sample is an important issue. For clinical samples containing cells, a cellular messenger RNA can be used as control to test the extracted material. Unsuccessful amplification of such message is indicative of lack of integrity of the messenger RNAs in that extract.

A number of control marker nucleic acid sequences are known in the state of the art. However, all these known markers exhibit the disadvantage that they are not markers that can be used universally for a large variety of types of cells. In addition, such markers are frequently expressed to such a high degree in the cells that their absence obviously is indicative of degradation but that their presence can still occur even though degradation has taken place of nucleic acid in the sample. Such degradation can however occur to an insufficient degree to ensure that all the marker nucleic acid has also been degraded. This latter aspect is naturally vital in the case of clinical diagnosis as this could lead to a false negative report of the presence of, for example, an infection or a tumor.

The importance of RNA detection in samples is increasing due to a number of discoveries where the presence of DNA in infections need not necessarily be clinically relevant. Infections considered to be latent may be detected with DNA analysis. For example, in the Journal of Medical Virology 42:164–169 (1994) by Velzing et al., the presence of cytomegalovirus (CMV) immediate early antigen (IEA) DNA and mRNA in peripheral blood leukocytes detected by PCR was investigated and related to the appearance of CMV pp65 antigen, CMV serology, and clinical status. In this test, keratin type I mRNA and the ssu rRNA gene served as internal controls. Two of seven seronegative samples were CMV EA positive. No relation was found between serology and the presence of CMV IEA DNA as determined in 37 samples. Five of 32 samples that could be analyzed were positive for CMV IEA mRNA of which four were also positive in the pp65 antigen detection technique. A clear relation was found between the presence of CMV IEA mRNA and CMV pp65 antigen in leukocytes and in the clinical findings as well. Velzing et al. concluded that detection of CMV mRNA may have a role in diagnosis of an active clinically relevant CMV infection. We have tested the same panel of patient samples and discovered different results, which is indicative that the presence of CMV IEA mRNA and CMV pp65 antigenicity are not related.

As human cytomegalovirus (CMV) infections are a major cause of morbidity and mortality in patients with decreased cellular immunity, such as recipients of organism transplants and patients with AIDS, the diagnosis of CMV infection often poses great challenges. Isolation of the virus is time consuming and may be unrelated to disease, since shedding of the virus frequently occurs. Also in particular the immune response is often delayed or even completely absent in immunocompromised patients so that reliance on a specific IgM response, commonly used for diagnosis of a primary CMV infection could therefore be difficult. In order to detect active viral replication, i.e the presence of active infection rather than latent infection, detection of mRNA specific for the virus should provide reliable test results. However, the problem still remains that RNA is extremely sensitive to degradation and therefore a negative result for RNA of a particular infectious organism has to be extremely reliable in order to exclude false negative results. The keratin I mRNA used in the Velzing et al. test is insufficient due to the fact it is not present in all cell types and, or in particular because it is expressed at quite a high level in cells. The advent of amplification technologies for nucleic acid means that very small amounts of nucleic acid can be detected. Sensitivities of 10 to 100 molecules of nucleic acid have been achieved with PCR and NASBA. Integrity control of such methods which are currently frequently used in diagnosis is therefore now becoming extremely important. As samples can be taken from a large number of species and various types of cells it would be preferable to devise a universal method of control that would be applicable on any type of sample. In particular in the case of diagnoses of diseases in humans it would be advantageous to have a test that could be applied to blood samples, biopties, cervical scrapes or any other samples taken of human tissue that comprise cellular mRNA.

The subject invention is therefore directed at a method for determining the integrity of nucleic acid isolated from a specimen of eukaryotic origin comprising subjecting the specimen to nucleic acid isolation followed by amplification using a pair of oligonucleotide primers in a manner known per se, said primers being capable of amplifying nucleic acid specific for RNA encoding a product of a housekeeping gene, said RNA being low abundance RNA, said gene being present in all cell types of a eukaryotic species and said method further comprises determining whether amplification of the nucleic acid specific for the RNA has occurred. In particular the method comprises amplifying mRNA. Optionally, the method can also comprise quantifying the amplification product. As this method is of particular relevance for diagnosis of diseases in humans the eukaryotic species is preferably a human being. The term housekeeping gene refers to a gene that is expressed in all cell types, due to the fact that it is involved in a process common to all cell types, i.e. must be a gene involved in a process common to all cell types. Another prerequisite for an improved method of control integrity of nucleic acid isolated from a eukaryotic species is that the control should not be present in a large amount in the cell in order for the method to have a high degree of sensitivity. Preferably, the marker to be used for testing the integrity of nucleic acid removed from a eukaryotic species should be present in an amount similar to or less than that of the nucleic acid to be detected.

What is required is a low abundance messenger RNA expressed to a degree lower than that of other known markers used for integrity control, such as keratin type I. A test of this can be easily carried out using a keratin type I comprising cell and comparing the amount of product resulting from an amplification reaction of keratin type I encoding mRNA and the mRNA to be used in the integrity control method of the subject invention. Another type of RNA which can be used as a control of degree of expression is β-actin mRNA which is expressed to a moderate degree. Other possibilities are human glyceraldehyde 3 phosphate dehydrogenase mRNA and factor V mRNA. The amplification reaction can comprise amplification of DNA or amplification of DNA in combination with RNA or simply comprise amplification of RNA. When using an amplification reaction wherein both DNA and RNA could be amplified one can destroy the DNA using DNase in a manner known per se prior to the amplification or one can select the amplification primers such that the amplified DNA and amplified RNA differ in length and composition due to the presence and absence of introns in order to discern between amplified chromosomal nucleic acid and nucleic acid amplified from mRNA. When using an ELGA detection method for example the difference in length of the amplified products should be at least 45 nucleotides. Therefore, the amplified sequence must comprise at least one exon—exon junction in order to discern between the amplified chromosomal nucleic acid and nucleic acid amplified from mRNA. As NASBA is a nucleic acid amplification method especially suited for RNA targets use of the NASBA amplification method is considered to be a preferred embodiment for carrying out the integrity control according to the subject invention. Preferably, it is also the method for the amplification of the RNA target for which the sample has to be tested. The preference for NASBA for testing is due to the fact that it is especially suited for RNA targets and amplification of intracellular RNA, such as ribosomal RNA or messenger RNAs from the cell itself or from invading organisms will often be involved. However, as prior to amplification these RNAs have to be extracted from the specimen to be tested and hence degradation of the RNA during this sample preparation or poor yields of RNA from the samples could lead to falsely negative NASBA results, the control of the integrity and the amount of RNA extracted from such specimens is necessary. Any method requiring the use of amplification usually means the nucleic acid to be determined is only present in minute quantities in the sample. With the subject method if degradation of 90% of e.g. actin mRNA occurred amplification would occur however if 90% of U1A mRNA were degraded no amplification will occur of U1A mRNA. Thus degradation of U1A mRNA will quickly lead to a negative result and thus warn of a potentially incorrect conclusion regarding the mRNA presence in the sample.

Particularly suited for application in the subject method are oligonucleotide primers specific for mRNA encoding a product of a housekeeping gene, said mRNA being low abundance mRNA, said gene being present in all cell types of eukaryotic species wherein the mRNA encodes a component of a small ribonucleoprotein (snRNP) particle. The small nuclear ribonucleoprotein (snRNP) particles are a family of low molecular weight RNA species, each complexed to a specific set of proteins. Although the exact function of the various snRNP particles is still largely unknown, the major snRNPs have been shown to be essential cofactors for mRNA processing reactions.

The U1 snRNP for example, one of the most abundant snRNPs is involved in the removal of introns and the splicing of exons from eukaryotic mRNA precursors (for reviews see Green, 1991; Guthrie, 1991). At least 10 proteins have been fould to be associated with the purified U1 snRNP particle and they can be divided into two classes. Seven of the Ul snRNP proteins are common proteins also present in other snRNPs. The three remaining proteins designated 70K, A and C, are U1 snRNP specific proteins.

The cDNAs of the U1 snRNP specific proteins have been cloned. This is described in Theissen et al. 86 (Theissen H. et al EMBO J. 5, 3209–3217 (1986), Spitz et al., 87 (Spitz R. A. et al. Nucl. Acids Res. 15, 10373–10391 (1987), Sillekens et al. 87 (Sillekens P. T. G. et al. EMBO J, vol. 6, no. 12, pp 3841–3848, 1987).

U2 snRNP comprises two specific proteins, A' and B", and U5 snRNP also has two candidates that appear to be specific proteins for such a particle. As low abundance is an important criterium of the mRNA to be selected for use in an integrity control method according to the invention a preference is expressed for mRNA exhibiting the lowest degree of expression.

The A protein of U1 snRNP is encoded by a low abundance mRNA expressed in humans from a single copy gene (Nelissen et al. 1991). Therefore, the U1 A protein encoding mRNA can be used as control mRNA in a preferred embodiment of the method according to the invention. Any other messenger RNA encoding the product of a housekeeping gene that is expressed to a similar degree or less is also useful in a method according to the invention.

Due to the homology that has been observed between the U1 A mRNA and the U2-B" mRNA it is preferable to employ either a primer specific for the non-homologous part of the U1 A mRNA to ensure amplification merely of the U1 A RNA without concomitant amplification of the U2-B" RNA. The homology at amino acid level is however no hindrance to applying the method according to the invention on any part of the nucleic acid sequence. In order to discern a difference between mRNA of A or B" it is not necessary to use primers for non-homologous regions. The nucleic acid sequences of A mRNA and B" mRNA are quite specific. As an alternative or concomitantly a detectable marker specific for the non homologous part of U1-A mRNA can be employed for detecting the amplified product. If it is used as an alternative, the primer can hybridize and/or recognize a part of the homologous part of the U1 A mRNA with the detectable marker recognizing and/or hybridizing to the non-homologous part. In the Nelissen et al. article of 1991 and the Sillekens et al. article of 1987 comparisons of the two sequences are given. In particular, exon 4 of U1-A is non-homologous to U2-B". In the cited articles the nucleotide sequences and the positions of the exons and introns are given as well as comparisons of U1-A amino acid and U2-B" amino acid sequences. The gen bank accession numbers for exon containing gene sequences I–VI are M60779–M60784, respectively and are incorporated herein by reference as is the data given in the Nelissen et al. and Sillekens et al. references. An embodiment for ensuring that the amplified sequence comprises a non-homologous nucleic acid sequence is a method wherein the amplified sequence comprises at least a part of exon 4 of U1-A. This can be achieved by amplification of nucleic acid using a primer upstream of exon 4 and a primer either in exon 4 or downstream of exon 4 such that the amplified sequence comprises at least a part of exon 4 and detection with a detectable marker specific for the part of exon 4 that has been amplified. The part of exon 4 that is amplified must be sufficiently long to be specifically recognized in this embodiment by the detectable marker. Alternatively, one primer can recognize a part of exon 4 and the other primer can recognize a part upstream of exon 4 with a detectable marker recognizing the amplified sequence or a part of the amplified sequence upstream of exon 4 but not upstream of said other primer. Another option comprises a primer recognizing a part of exon 4, the other primer recognizing a sequence downstream of exon 4 such that the amplified sequence comprises at least a part of exon 4 and a detectable marker either recognizing a part of exon 4 that has been amplified or a part of the nucleic acid sequence downstream of exon 4 that has been amplified. The various options open for selection of oligonucleotide primers and detectable markers will be obvious to a person skilled in the art.

It is also possible to amplify the nucleic acid using primers that recognize both U1-A and U2-B" mRNA but as the sequences of both products are known the length of the amplified sequences can be accurately predicted and it can be readily determined which amplification sequence signal belongs to which product. It will however incorporate the least amount of work and the easiest detection of signal when primers are selected such that the amplified sequence can only be detectable if it is a sequence specific for U1-A. This can be achieved either by a detection method specific for RNA specific for U1-A or specific amplification of only a sequence specific for U1-A.

A method according to the invention can thus be carried out when the pair of oligonucleotide primers is selected such that the amplified sequence comprises at least one exon-exon junction. As is stated previously this is to ensure that upon amplification of both chromosomal nucleic acid and mRNA the difference in length of amplified product due to the presence or absence of the intermediate intron is apparent.

The method according to the invention can be carried out in a suitable manner when the amplified sequence comprises at least a part of a nucleic acid sequence corresponding to exon 4 of the nucleic acid sequence encoding U1- snRNP protein A (U1A). The amplified sequence can comprise at least the exon 3 - exon 4 junction of nucleic acid sequence encoding U1 snRNP A (U1A). Another alternative is that the amplified sequence comprises at least the exon 4 -exon 5 junction of the nucleic acid sequence encoding U1-snRNP A (U1A).

The method according to the invention also comprises a detection step of the amplified sequence. The detectable marker that can be used can be a sequence, capable of hybridizing specifically to a part of the amplified sequence. As already indicated above such a detectable marker can be capable of hybridizing to part of exon 4 or it can be capable of hybridizing to a sequence upstream of exon 4 should this have been amplified with a primer located upstream of exon 4 or can be a sequence capable of hybridizing to a sequence downstream of exon 4 if the primer has been selected for hybridizing to a sequence downstream of exon 4. The detectable marker will recognize a sequence located somewhere between the two recognition sites of the primers used in the amplification reaction. Preferably, either one of the primers employed or the detectable marker will be capable of specifically recognizing a part of the nucleic acid sequence of exon 4. Preferably, at least one of the primers and/or the detectable marker will then also be specific for a part of the amplified sequence upstream or downstream of exon 4 of the mRNA, i.e. also specifically recognizing a part of an exon other than exon 4. Mutatis mutandis in the above and following exons (3), (4) and (5) may be read as exons (n−1), (n) and (n+1), wherein n is an integer indicative of the exon number for the RNA to be detected.

The invention is also directed at an integrity control kit for nucleic acid of eukaryotic origin comprising a pair of oligonucleotide primers, said primers being capable of amplifying nucleic acid in a manner known per se, said nucleic acid being specific for mRNA encoding a product of a housekeeping gene, said mRNA being low abundance mRNA, said gene being present in all cell types of a eukaryotic species, said eukaryotic species preferably being a human being. Such a kit will further comprise a detectable marker of the amplified sequence. The detectable marker of the kit according to the invention or for use in the method according to the invention can suitably be an oligonucleotide sequence capable of hybridizing to the amplified sequence. The detectable marker can also be an antibody capable of specifically recognizing the amplified sequence. The detectable marker can be provided with a label that is detectable as is common in the state of the art for markers of nucleic acid sequences, e.g. an enzyme, a chromogenic substrate, a radio isotope, a fluorescent group etc. Also the detectable marker can be capable of specifically immobilizing the amplified sequence in a manner known per se followed by detection of the immobilized amplified sequence in a manner known per se with or without a rinsing step and using a further compound binding to the immobilized sequence and subsequently providing a detectable signal. The execution of this type of tests is routine to a person skilled in the art of nucleic acid detection. The kit will comprise primers and detectable marker in a combination such that either only the amplified sequence to be detected is present in the sample or else a combination of amplified sequences is present but the detectable marker will only detect the amplified sequence to be detected. The combinations that are suitable can easily be ascertained upon comparison of the nucleic acid sequences known for housekeeping genes in particular for mRNA encoding components specific for small nuclear ribonucleoprotein particles, preferably major small nucleair ribonucleoprotein particles, and in particular components of the major small nucleair ribonucleoprotein particle U1-snRNP, such a component for example being protein A. Preferably, a kit according to the invention comprises a pair of oligonucleotide primers capable of amplifying mRNA encoding a product of a housekeeping gene, said mRNA being low abundance mRNA, said gene being present in all cell types of a eukaryotic species. In particular when a kit according to the invention is to be used for amplifying both DNA and RNA the pair of oligonucleotide primers is selected such that the amplified sequence comprises at least one exon-exon junction. When the amplified sequence encodes U1-snRNP protein A, preferably the amplified sequence comprises at least a part of a nucleic acid sequence corresponding to exon 4 of the nucleic acid sequence encoding U1-snRNP protein A and the primers are selected appropriately. A suitable kit according to the invention can thus comprise primers selected such that the amplified sequence comprises at least the exon 3 - exon 4 junction of the nucleic acid sequence encoding U1-snRNP A. Another suitable embodiment comprises a kit wherein the primers have been selected such that the amplified sequence comprises at least the exon 4 - exon 5 junction of the nucleic acid sequence encoding U1-snRNP A. This means that either one of the primers comprises a sequence capable of hybridizing to a part of exon 4 of the nucleic acid sequence encoding U1-snRNP A or one primer comprises a sequences downstream of exon 4 and the other comprises a sequence upstream of exon 4. A suitable embodiment of a kit according to the invention can comprise a detectable marker capable of specifically detecting a part of the nucleic acid sequence of exon 4 of the nucleic acid sequence encoding U1-snRNP A with the oligonucleotide primers being selected such that the amplified sequence comprises at least a part of the nucleic acid sequence encoding exon 4, that the detectable marker recognizes, said primer being selected such that the amplified sequence comprises the nucleic acid sequence located between the recognition sites of the primers. A kit according to the invention can comprise an oligonucleotide primer pair comprising a primer capable of recognizing a part of exon 3 of the nucleic acid sequence encoding U1-snRNP A and a primer capable of recognizing part of the nucleic acid sequence of exon 4 of the nucleic acid sequence encoding U1-snRNP A and/or capable of recognizing part of the nucleic acid sequence downstream of exon 4 of the nucleic acid sequence encoding U1-snRNP A, said primer pair being selected such that the amplified sequence comprises the nucleic acid sequence located between the recognition sites of the primers.

In the examples given the method according to the invention has been applied to isolation of total nucleic acid from cultured cells, isolation of total nucleic acid from blood, isolation of total nucleic acid from cervical scrapings to illustrate the applicability of the method on samples of differing cell types of eukaryotic origin.

The requirements to be made for the oligonucleotide primers and detectable marker to be used in the amplification reaction of the method according to the invention will be obvious to a person skilled in the art. The normal requirements for amplification reaction primers and markers regarding degree of homology and applied hybridisation conditions are in force. This means in general terms a primer will comprise at least 10 nucleotides capable of hybridising to a corresponding part of the sequence to be amplified under normal to stringent conditions. The requirements can be found in a handbook of molecular cloning (e.g. Sambrook et al. (Sambrook, J. Fritsch, E. F., Maniatis T. (1989) Molecular Cloning. A laboratory manual. Second ed. Cold Spring Harbor Laboratory Press, Cold Spring Harbor, N.Y.)). In a preferred embodiment the oligonucleotide probe will be selected to exhibit a degree of homology ensuring the most reliable result at a reasonable cost. Optimum results are in general obtained when the homology is 100% and the oligonucleotide probe has a length of 15 to 25 oligonucleotides. When using NASBA the amplified sequence i.e. the product is the complementary strand, thus the oligonucleotide for detecting the amplified product will correspond to the sequence of the original nucleic acid. When using PCR the amplified sequence i.e. the product is a double stranded DNA and detection can occur of either strand. Thus the oligonucleotide used for detection of amplified product may hybridize to either the coding strand or the complementary strand of nucleic acid to be amplified. We hereby cite some general references illustrative of the PCR methodology. The content thereof related to carrying out PCR reactions is hereby enclosed (PCR Technology, J. A. Ehrlich, ed., Stockholm Press, New York (1989); Molecular Methods for Virus Detection, D. L. Wiedbrauk and D. H. Farkas, eds., Academic Press, New York (1995). Nucleic Acid Hybridisation, B. D. Hames and S. J. Higgins, eds., IRL Press, Oxford, Washington D.C. (1985).

The method and kit according to the invention are in particular useful when the absence of a nucleic acid sequence has to be determined with a high degree of certainty, in particular for diagnosis of malignancies and infections with pathogens, most particularly for diagnosis of active infections.

In general at any time after isolation of a nucleic acid sequence from a eukaryotic sample the method according to the invention can be carried out on said sample. The presence of the amplifiable nucleic acid comprising a sequence specific for mRNA encoding a product of a housekeeping gene, said mRNA being low abundance mRNA and said gene being present in all cell types of a eukaryotic species will be indicative of integrity of RNA in the sample and, consequently, concomitant absence of the nucleic acid sequence to be detected can with a high degree of certainty be indicative of a negative sample. Absence of the nucleic acid comprising a part of the nucleic acid sequence specific for mRNA encoding a product of a housekeeping gene, said mRNA being low abundance mRNA, said gene being present in all cell types of a eukaryotic species is indicative of degradation of nucleic acid and implies that the sample cannot be considered reliable if a negative result of the sequence to be detected is ascertained or if the nucleic acid sequence to be determined was quantitatively analysed. Evaluation of quantitative results could provide interesting information with regard to management of patients undergoing for example antiviral therapy. RNA diagnosis can also be extremely relevant with regard to the field of oncology. Tumor cells are often distinguished from normal cells by a different pattern of expression. Genes that are not expressed in normal cells or are expressed at a low level are often expressed at a higher level in tumor cells. Furthermore, in various kinds of viral infections a so called window period is known to exist. This window period comprises the period between becoming infected and the actual development of antibodies by the infected body. In particular diagnosis during this period requires nucleic acid diagnosis.

The method according to the invention can thus provide information about the quality of the nucleic acid isolated and also the efficiency of the isolation. It will be important for deciding whether a clinical sample is truly negative for a specific nucleic acid target or whether it is negative due to nucleic acid degradation taking place during any of the sample treatments prior to the integrity control amplification and detection method of the subject invention.

DESCRIPTION OF THE FIGURES

FIG. 1: Oligonucleotides for amplification and detection of the human U1A mRNA exon 3/exon 4 junctional region.

FIG. 3: Human U1A mRNA detection in nucleic acid extracts from cultured cell lines. Total nucleic acid was extracted from nine in vitro cultured human or human x mouse cell lines and analysed for the presence of U1A mRNA by NASBA amplification. Amplified products were analysed by Northern blotting with probe snRNP-U1A RA1 (Table 1). Lanes: (1) Uc729; (2) HCV HuOT 01; (3) HCV HuOT 02; (4) Tox HuOT 01; (5) K14; (6) K6H6B5; (7) Tox HuOT 28; (8) HeLa cells infected with Chlamydia trachomatis; (9) HELF cells infected with Cytomegalovirus. Controls: $(10^4)$-$(10^1)$ 10-fold dilution series of in vitro generated U1A RNA; (NT) no template NASBA reactions.

EXAMPLES

MATERIALS AND METHODS

Plasmids

Figure 2A:
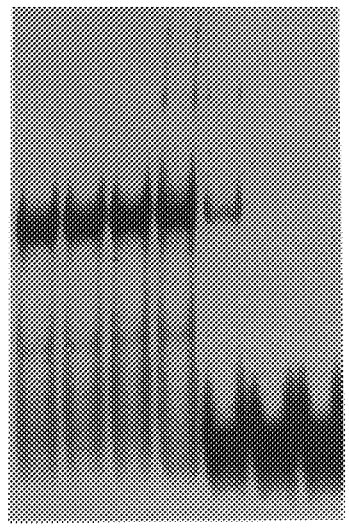
FIGS. 2A and 2B: Sensitivity of the human U1A mRNA NASBA assay. In vitro generated RNA was amplified from a 10-fold dilution series and the amplified product was analysed by enzyme-linked gel assay (ELGA) (A) or agarose gel electrophoresis and Northern blotting (B) with probes snRNP-U1A HRP1 or snRNP-U1A RA1 (Table 1), respectively. Lanes: (1) $10^5$ molecules; (2) $10^4$ molecules; (3) $10^3$ molecules; (4) $10^2$ molecules; (5) $10^1$ molecules; (6), (7) no template NASBA reactions.

A cDNA fragment containing the entire coding sequence of the human U1 snRNP-specific protein A was obtained by digestion of the plasmid pHA4 (Sillekens et al., 1987) with restriction enzymes NcoI and BamHI. Subsequent ligation of the fragment into NcoI/BamHI-digested T7 expression vector pET3a (Studier et al., 1990) revealed the plasmid pET3a/U1A-cDNA.

RNA transcription.

To generate in vitro RNA, plasmid pET3a/U1A-cDNA was linearized by BamHI digestion. Digested DNA was purified by phenol extraction and concentrated by ethanol precipitation. Transcription from the linearized plasmid DNA was performed in transcription buffer [40 mM tris-hydrochloric acid (pH 7.5); 6 mM magnesium chloride; 2 mM spermidine; 10 mM sodium chloride] supplemented with 2.5 mM of each rNTP, 10 mM dithiothreitol (DTT), 1 unit per ml RNA Guard (Pharnacia), and 60–70 units T7 RNA polymerase (Pharmacia). After incubation for two hours at 37° C., DNase I (Boehringer) was added to a final concentration of 0.25 unit per ml and the reaction mixture incubated at 37° C. for an additional 15 minutes.

The resulting in vitro RNA was quantitated by slot blot hybridisation. A two-fold dilution series of the RNA was slot blotted together with a dilution series of oligonucleotide snRNP-U1A RA2 (Table 1) comprising part of the exon 4 sequence of the U1A protein gene (FIG. 1). Concentration of the oligonucleotide dilution series was determined by $A_{260}$ measurement. The slot blot was hybridized to oligonucleotide snRNP-U1A RA1 complementary to the blotted oligonucleotide and the in vitro RNA (Table 1) and labelled at its 5'-end by using T4 polynucleotide kinase (Pharmacia) and [gamma-$^{32}$P]ATP. By comparison of the signals of the known amounts of oligonucleotide on the blot and the signals obtained with the RNA dilutions, the amount of RNA molecules present in the original in vitro RNA stock could be estimated.

Isolation of total nucleic acid from cultured cells.

For nucleic acid isolation from cells cultured in vitro, a total of about $2 \times 10^5$ cells was suspended in 1 ml of Lysis buffer [50 mM tris-hydrochloric acid (pH 6.4); 20 MM EDTA; 1.3% (w/v) Triton X-100; 5.25M Guanidinium thiocyanate]. To the lysed cell suspension 70 μl of hydrochloric acid-activated silicium dioxide particles [size-selected suspension of 1 mg/ml in 0.1M hydrochloric acid (Sigma); see ref. Boom et al., 1990] were added and the suspension was incubated during 10 minutes at room temperature with regular vortexing. Nucleic acid bound to the silica was spun down by centrifugation. Pelleted silica particles were washed twice with 1 ml GuSCN wash buffer [50 mM tris-hydrochloric acid (pH 6.4); 5.25M guanidinium thiocyanate], followed by two washing steps with 1 ml 70% ethanol and a single washing step with 1 ml acetone. After each washing step, the suspension was briefly centrifuged and the silica pellet was resuspended in the next washing solution by thorough mixing. After removal of the acetone, the silica particles were dried by incubation at 56° C. in a heating block during 10 minutes. Nucleic acid was eluted from the silica particles by incubation in 100 μl distilled water at 56° C. during 10 minutes. Finally, the silica particles were spun down again and the supernatant was carefully pipetted into fresh reaction tubes avoiding any carry-over of silica. Extracted nucleic acid samples were stored at −70° C. until use.

Isolation of total nucleic acid from blood.

Ethylenediaminoacetic acid (EDTA) or heparin anticoagulated blood was mixed with 9 volumes of Lysis buffer within a few hours after bleeding and stored at −70° C. until being thawed for nucleic acid isolation. From 5 μl of these whole blood samples in Lysis buffer nucleic acid was isolated by adding 70 μl of silica suspension and following the protocol as described for nucleic acid isolation from cultured cells.

Isolation of total nucleic acid from cervical scrapings.

Epithelial cells of the cervical region were collected using an Ayre spatula. The scraped material was placed immediately in a tube containing 5 ml of Lysis buffer and thoroughly mixed by vortexing. Samples were stored at −70° C. until use. After thawing and the addition of 70 μl of silica suspension, nucleic acid was isolated as described for cultured cells.

NASBA amplification.

The primer set used in the NASBA was designated to detect part of the exons 3 and 4 junctional region of the U1A mRNA sequence. Sequences, polarity, and locations of the primers and of the probes used for specific detection, are shown in FIG. 1. To set up an amplification reaction, 10 μl of 2.5×reaction buffer [100 mM tris-hydrochloric acid (pH8.5); 30 mM magnesium chloride; 175 mM potassium chloride; 12.5 mM dithiothreitol; 2.5 mM of each dNTP; 5 mM of ATP, CTP, and UTP; 3.75 mM of GTP; 1,25 mM of ITP] was added to a reaction tube together with 6.25 μl 4×primermix [0.8 mM of each primer; 60% dimethylsulphoxide], 5 μl nucleic acid solution, and 1,75 μl destined water. This mixture was heated at 65° C. during 5 minutes, after which the tubes were placed at 41° C. Two microliters of enzyme mix [40 units T7 RNA polymerase; 8 units AMV reverse transciptase; 0.1 unit RNase H; 1.25 mg/ml BSA] were added and the contents of the tube were mixed by gentle tapping. The reaction was incubated at 41° C. for 90 minutes and stopped by placing it at −20° C. Northern blot analysis of NASBA products.

Amplified RNA was transferred from a 2.0% pronarose gel (Hispanagar, S. A.) to a nylon membrane (Zeta-probe, BioRad, USA) by vacuum blotting in 2×SSC [1×SSC is 150 mM sodium chloride; 15 mM sodium citrate] during 2 hours. Membranes were preincubated at 50° C. in a hybridization solution [0.5M sodium phosphate (pH 7.2); 7% sodium dodecyl sulphate] during 30 minutes prior to the addition of 5'-$^{32}$P-end-labelled oligonucleotide probe snRNP-U1A RA1 (Table 1) to a final concentration of about $10^5$ cpm/ml. Hybridization was performed overnight at 50° C. Subsequently washings were carried out at 50° C. in 0.3×SSC supplemented with 0.1% SDS. Autoradiography was performed for several hours at −70° C. with Kodak Royal X-omat film and intensifying screens.
Enzyme-linked gel assay (ELGA).

For non-radio-active detection of amplified RNA a rapid "in-solution" hybridisation assay was developed. Hybridisation of the NASBA product to a specific horseradish peroxidase (HRP) 5'-labelled oligonucleotide probe was performed by mixing 2 μl of a NASBA reaction with 1 μl 5×SSC, 1 μl concentrated loading buffer [25% (v/v) glycerol; 10 mM sodium phosphate buffer (pH 7.0); 0.05% bromophenol blue; 0.01% xylene cyanol], and 1 μl HRP-labelled oligonucleotide snRNP-U1A HRPI (Table 1) stock solution (containing about $10^{10}$ molecules per μl), followed by incubation at 45° C. during 15 minutes. After hybridisation, half of the reaction mixture was directly applied onto a 7% polyacrylamide gel supplemented with 0.04% (w/v) dextrane sulphate. After separation of bound and unbound HRP-labelled oligonucleotide by electrophoresis, the probe was visualized in the gel by direct staining with 50 ml substrate solution [125 mg 3,3', 5,5'-tetramethylbenzidine per ml; 0.003% hydrogen peroxide; 100 mM sodium citrate buffer (pH 5.2)] for about 10 minutes at room temperature. Finally, the gel was fixed by overnight incubation in a 50% (v/v) methanol solution and air dried.

EXAMPLE 1
Analytical sensitivity of U1A mRNA NASBA.

Figure 2B:
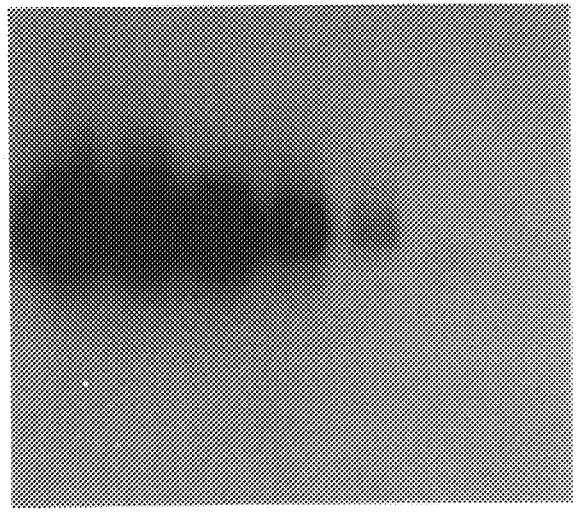

To assess the analytical sensitivity of the primer set snRNA-U1A 1.1/snRNP-U1A 2.2 designed for amplification of part of the U1 snRNP-specific A (U1A) protein mRNA (Table 1, FIG. 1), an RNA template of known sequence and concentration was prepared by in vitro transcription of a cloned 1.2 kb cDNA fragment of the target (Sillekens et al., 1987). A standard dilution series of the in vitro generated RNA was made and these dilutions were used to test the detection sensitivity of the amplification assay. As shown in FIG. 2, under optimized conditions an input as low as 10 molecules revealed amplification of the anticipated RNA. However, since the detection of 10 molecules was not reproducibly possitive, the detection level in the model system with in vitro generated RNA should be considered as 10–100 molecules of input RNA.

EXAMPLE 2
Detection of U1A mRNA in cell cultures.

In a first attempt to evaluate the U1A mRNA NASBA primer set on clinical specimens, total nucleic acid isolation from several cell lines cultured in vitro was used as input material. Efficiency of amplification was monitored by simultaneous amplification of a dilution series of in vitro generated U1A RNA. In this series of NASBA reactions 10 molecules of input RNA could still be detected (FIG. 3, lanes $10^4$-$10^1$). In the human tumor cell line Uc729 and in the Epstein-Barr virus (EBV) transformed human B-cell lines HCV HuOT 01, HCV HuOT 02, Tox HuOT 01, and K14 the presence of U1A mRNA could unambiguously be demonstrated (FIG. 3, lanes 1–5).

TABLE 1

U1A mRNA oligonucleotides

| Amplification | Sequence |
| --- | --- |
| snRNP-U1A 1.1 | 5'-aattctaatacgactcactatagggagaGGCCCGGCATGTGGTGCATAA-3' SEQ ID NO:1 |
| snRNP-U1A 2.2 | 5'-CAGTATGCCAAGACCGACTCAGA-3' SEQ ID NO:2 |

| Detection | Sequence |
| --- | --- |
| snRNP-U1A RA1 | 5'-GCATGCCGCCGATGACTCA-3' SEQ ID NO:3 |
| snRNP-U1A RA2 | 5'-TGAGTCATCGGCGGCATGC-3' SEQ ID NO:4 |
| snRNP-U1A HRP1 | 5'-X—AGAAGAGGAAGCCCAAGAGCCA-3' SEQ ID NO:5 |

X = NH$_2$-group

Nucleic acid extracted from HeLa cells infected in vitro with Chiamydia trachomatis serovar L2 or from human embryonic lung fibroblast (BELF) cells infected with CMV (laboratory strain AD169) was also analysed for the presence of U1A mRNA. In either case amplimer derived from the target could be detected and its nature confirmed by Northern blotting (FIG. 3, lanes 8, 9).

EXAMPLE 3
Detection of U1A mRNA in whole blood.

Whole blood or blood components are frequently used as the principal material in diagnostic assays. For the identification of human cytomegalovirus (HCMV) viremia, for instance, peripheral blood leucocytes (PBLs) are often used for the detection of HCMV-specific nucleic acid. The clinical significance of the presence of HCMV DNA in white blood cells is restricted since detection of the DNA in PBLs does not necessarily reflect viral replication (Gerna et al., 1991). In contrast, transcription of the viral genome is associated with viral replication and, hence detection of viral transcripts should allow reliable diagnosis of systemic active HCMV infection. Therefore, monitoring of the integrity of RNA extracted from blood is a necessity.

Figure 4A:
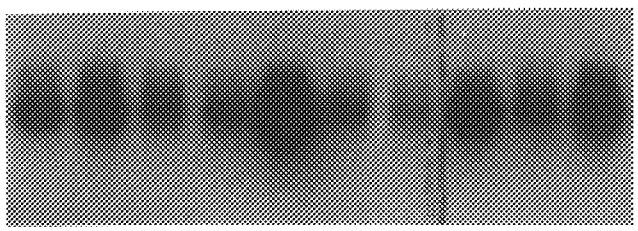
FIG. 4: Human U1A mRNA detection in nucleic acid extracts from whole blood samples. Total nucleic acid was extracted from ten EDTA-anticoagulated whole blood samples and analysed for the presence of U1A mRNA by NASBA amplification. Amplified products were analysed by Northern blotting with probe snRNP-U1A RA1 (Table 1). Lanes: (1)–(10) patient samples. Controls $(10^4)$-$(10^1)$ 10-fold dilution series of in vitro generated U1A RNA; (NT) no template NASBA reactions.
Figure 4B:
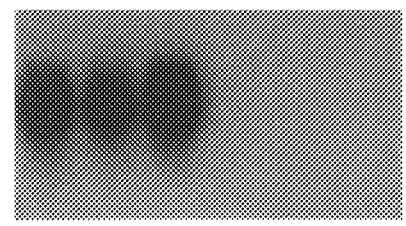

From thirty-seven blood samples obtained from patients clinically at risk of infection with HCMV, nucleic acid was isolated. Prior to the detection of HCMV RNAs in these isolates, the quality of the extracted RNA was validated. Analysis of the samples for the presence of amplifiable U1A protein mRNA in all cases revealed amplimer that was identified by Northern blotting. Representative results for ten of these samples are shown in FIG. 4. Despite the fact that the intensity of the signals varies, presence of intact U1A mRNA in all samples was obvious. Sensitivity of the assay was 100 U1A RNA molecules (FIG. 4, lanes $10^4$-$10^1$).

EXAMPLE 4
Detection of U1 A mRNA in cervical scrapes.

Infections of the genital tract by human papillomavirus (HPV) or Chlamydia trachomatis can be recognized by identification of DNA or RNA sequences of these infectious agents in cells obtained from the infected tussue. Cervical scrapings are frequently used as the starting material in these assays.

Figure 5A:
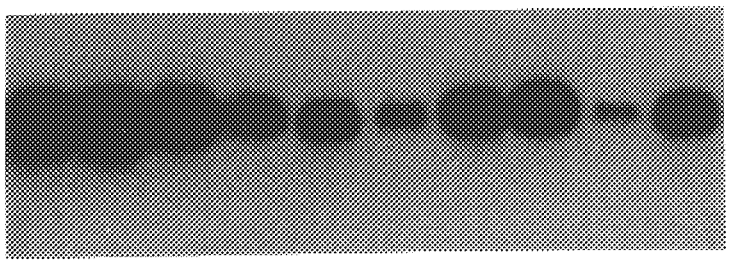
FIG. 5: Human U1A mRNA detection in nucleic acid extracts from cervical scrapings. Total nucleic acid was extracted from ten cervical scrapings and a cultured human cell line and analysed for the presence of U1A mRNA by NASBA amplification. Amplified products were analysed by Northern blotting with probe snRNP-U1A RA1 (Table 1). Lanes: (1)–(10) patient samples. Controls: (K14) cultured human cell line; (NT) no template NASBA reactions.
Figure 5B:
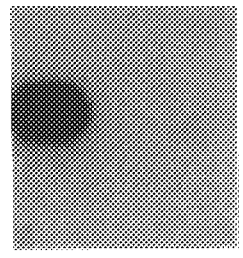

The finding that many primary cervical tumors harbour specific HPV genotypes (Dürst et al., 1983; van den Brule et al., 1993) supports a causal relationship between certain HPV types and squamous cell carcinoma of the genital tract. Expression of certain regions of the HPV genome might be involved in the development of these carcinoma. Therefore, monitoring of the presence of transcripts from these regions could be of prognostic value with respect to tumor progression. Nucleic acid was extracted from cervical scrapings of women attending an outdoor clinic for sexually transmitted diseases. Quality of the RNA in the extracts was verified by U1A mRNA NASBA. FIG. 5 shows the results of the analysis of ten cervical scrapings. The presence of U1A mRNA could be demonstrated in all samples.

Figure 6A:
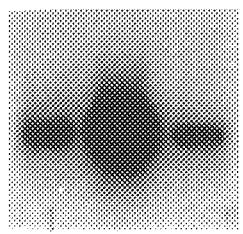
FIG. 6: Human U1A mRNA detection in nucleic acid extracts from cervical scrapings of Chlamydia trachomatis infected woman. Total nucleic acid was extracted from cervical scrapings of three women with a positive Chiamydia trachomatis serology and analysed for the presence of U1A mRNA by NASBA amplification. Amplified products were analysed by Northern blotting with probe snRNP-U1A RA1 (Table 1). Lanes: (1)–(3) patient samples. Controls ($10^4$)-($10^1$) 10-fold dilution series of in vitro generated U1A RNA; (NT) no template NASBA reactions.
Figure 6B:
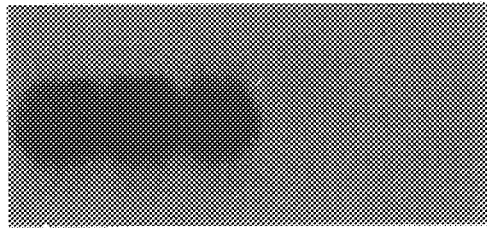

For Chlamydia trachomatis 16S ribosomal RNA (rRNA) is an appealing target to diagnose an infection with this organism because of the high expression levels of this RNA. This makes 16S rRNA easier to detect than other targets occuring in much lower copy numbers. Furthermore, identification of all three Chlamydia species, Chlamydia trachomatis, Chlamydia psittaci, and Chlamydia pneumoniae, is possible by amplification of a stretch of the 16S rRNA with a genus-specific primer set. Therefore, verification of the RNA integrity also is of importance for Chlamydia trachomatis NASBA assays. Since the Chlamydiaceae are a family of obligate intracellular bacteria, integrity of RNA extracted from cervical or urethral swabs can be verified by amplification of a cellular RNA target like the U1A mRNA. Nucleic acid was extracted from four cervical scrapes that had been taken without any necessary precautions to avoid RNA degradation. All four samples proved positive for Chlamydia trachomatis in a PCR assay targeting for the endogenous plasmid. However, in a 16S rRNA NASBA assay only two samples were found positive. Validation of the RNA in these samples by U1A mRNA NASBA revealed that neither of the isolates contained amplifiable target rnRNA (data not shown). In a second study, nucleic acid was isolated from three clinical samples obtained from patients with a positive Chlamydia trachomatis serology under conditions more suited for RNA isolation. When these isolates were analyzed for the presence of intact U1A mRNA, all three were positive (FIG. 6, lanes 1–3). Subsequent analysis for Chlamydia 16S rRNA by NASBA also revealed the presence of this RNA target in all samples.

EXAMPLE 5
Materials and methods.
Clinical samples
Whole blood samples (From the Central Laboratory of the Netherlands Red Cross Blood Transfusion service (CLB) in Amsterdam (Dr. Th. M. Cuypers)), two series of ethylenediaminoacetic acid (EDTA) anticoagulated whole blood samples, each mixed with 9 volumes of Lysis buffer [50 MM tris-hydrochloric acid (pH 6.4); 20 mM EDTA; 1,3% (w/v) Triton X-100, 5.25M guanidinium thiocyanate], were obtained. The first series consisted of whole blood samples from two individuals that were mixed with the Lysis buffer after deliberate incubation at room temperature for different periods of time (table 2). Prior to the addition of Lysis buffer, an aliquot of each sample was used to count the intact leukocytes still present in the specimen after each incubation period. Cell counts were performed using a Coulter-counter. Furthermore, an estimate of the percentage of granulocytes and lymphocytes after each incubation interval was made by differentiating 100 cells of each sample. After addition of Lysis buffer, samples were frozen and stored at −70° C. until use.

TABLE 2

Whole blood samples for preservation study of U1A mRNA

| Time (hours) | Cells ($10^6$/ml) | Granulocytes | Lymphocytes (%) |
|---|---|---|---|
| Donor A | | | |
| 0 | 7.5 | 63 | 37 |
| 6 | 7.4 | 52 | 48 |
| 16 | 7.5 | 59 | 41 |
| 24 | 7.5 | 60 | 40 |
| 48 | 6.6 | 9 | 91 |
| 70 | 5.6 | 16 | 84 |
| 115 | 4.6 | 4 | 96 |
| 163 | 5.0 | 0 | 100 |
| Donor B | | | |
| 0 | 6.0 | 72 | 28 |
| 6 | 5.9 | 82 | 18 |
| 16 | 6.2 | 77 | 23 |
| 24 | 6.0 | 76 | 24 |
| 48 | 5.3 | 31 | 69 |
| 70 | 4.5 | 34 | 66 |
| 115 | 3.7 | 0 | 100 |
| 163 | 3.8 | 0 | 100 |

The second series consisted of whole blood donations from 12 individuals that were mixed with 9 volumes of Lysis buffer as soon as possible after bleeding. Also for these samples a total cell count and an estimate of the percentage of granulocytes and lymphocytes was made. Lysates were stored at −70° C. until use.

RESULTS

U1A mRNA preservation in blood cells.

Figures 7A, 7B:
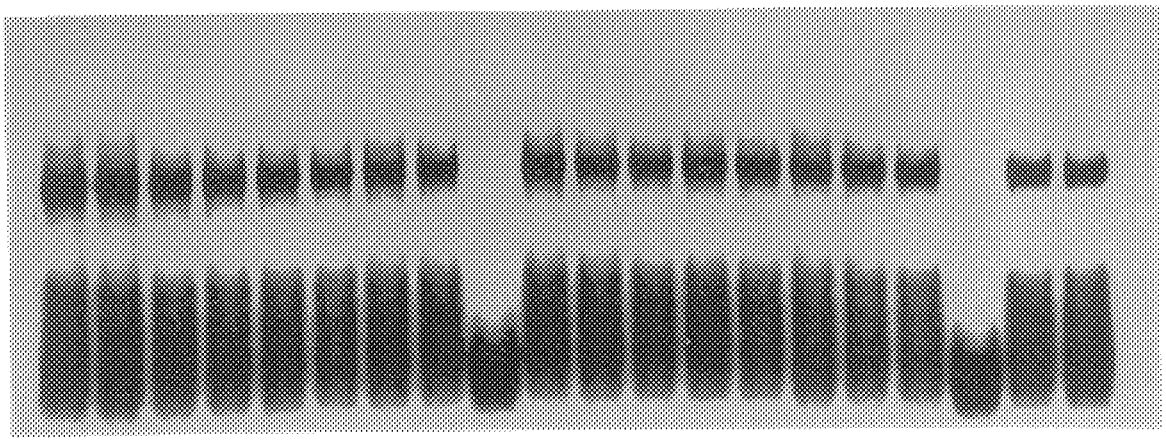
FIGS. 7A and 7B: Preservation of U1A mRNA in whole blood samples. Nucleic acid was isolated from whole blood samples stored at room temperature for variable periods of time. Extracted nucleic acid was analysed for the presence of amplifiable U1A mRNA by NASBA (System format) followed by ELGA detection with probe snRNP-U1A HRP1. Panels (A) and (B) represent preservation series of two individuals. Lanes (1) t=0; (2) t=6 hr; (3) t=16 hr; (4) t=24 hr; (5) t=48 hr; (6) t=70 hr; (7) t=115 hr; (8) t=163 hr; (9) no template. Controls ($10^3$)-($10^2$) ten-fold dilution series of in vitro generated U1A RNA.

Since blood samples are subjected to different physical conditions in daily laboratory practice, the influence of the time between bleeding and addition of Lysis buffer was investigated. EDTA-blood was obtained from two individuals and left at room temperature. A sample of each donation was added to Lysis buffer at the time of bleeding. The remaining blood volumes were stored at room temperature and at regular time intervals (see table 2) a sample was taken, added to Lysis buffer and stored at −70° C. until use. After collection of all the samples, nucleic acid was isolated from 100 µl blood equivalents and tested for the presence of intact U1A mRNA. Despite the vast reduction of the number of intact granulocytes between 24 and 48 hours after bleeding (table 2), U1A RNA can still be amplified from these whole blood samples, even after storage for 168 hours at room temperature (FIG. 7). Most likely, this is due to the lymphocytes of which a relatively fair amount remains intact under these conditions.

Expression level of U1A mRNA in leukocytes.

In the most ideal situation, Integrity Control RNA is expressed at a lower level than the target of interest. However, in case this target is not present in all cells of the specimen, a situation that can be encountered when analysing a viral or bacterial intracellular target in a sample in which not all cells are infected, the total amount of Integrity Control RNA should not exceed the number of target RNAs too much. Therefore, as Integrity Control a RNA target should be chosen with a low expression level.

Figures 8A, 8B:
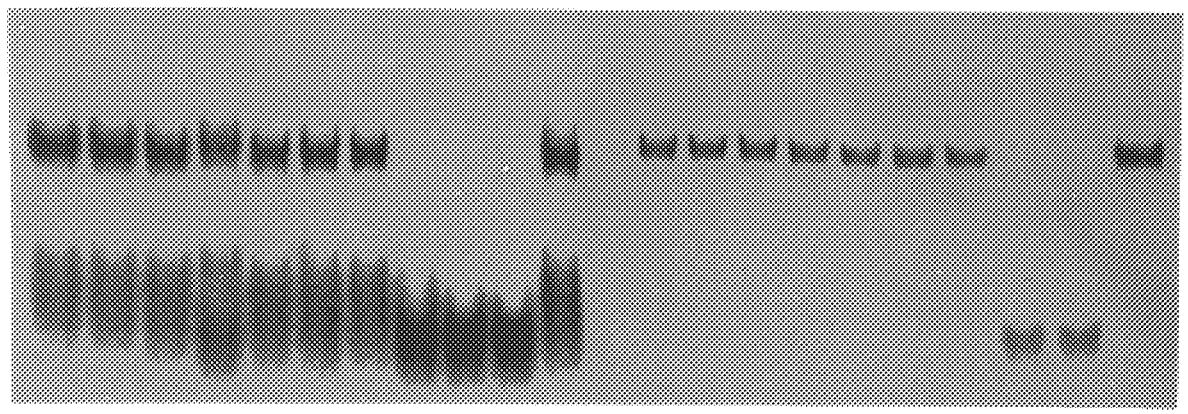
FIG. 8: End-point dilution for U1A mRNA and Factor V mRNA in nucleic acid extracted from whole blood. Nucleic acid was isolated from a whole blood sample (table 3, donor B, t=0). Three-fold dilution series of the extracted nucleic acid were tested for U1A mRNA and Factor V mRNA by NASBA (System format) and analysed with ELGA. Lanes: (1) undiluted; (2) 3-fold dilution; (3) 9-fold dilution; (4) 27-fold; (5) 81-fold; (6) 243-fold; (7) 729-fold; (8) 2187-fold; (9) 6561-fold; (10) 19.683 fold. Controls: ($10^2$) 100 molecules of in vitro generated U1A RNA or Factor V RNA.

To get an indication of the expression level of U1A mRNA in leukocytes, the number of mRNA copies per cell was estimated from a limiting dilution series of nucleic acid extracted from a whole blood sample with a known cell count. A 3-fold dilution series of nucleic acid extracted from the blood sample of donor B of the U1A mRNA preservation study added to Lysis buffer immediately after bleeding (table 2, donor B, t=0) was analysed for U1A mRNA. The 729-fold diluted sample was found to be the end-point dilution for U1A mRNA (FIG. 8). The number of leukocytes in the original whole blood sample was $6 \times 10^6$ cells/ml. An equivalent of 5 µl whole blood and serial dilutions thereof were tested. Therefore, 5 µl of a 729-fold dilution contains total RNA extracted from about 40 cells assuming 100% recovery of RNA during nucleic acid extraction. With a lower detection limit of 100 molecules U1A RNA in NASBA, a rough estimate of the expression level of U1A mRNA in leukocytes would be several copies per cell.

Detection of U1A rnRNA versus other intracellular targets.

Detection of U1A mRNA was compared to the detection of other intracellular RNA targets in dilution series of nucleic acid extractions of whole blood samples. In a first experiment, the limiting dilution series used for estimation of the U1A mRNA in leukocytes was also analysed for Factor V mRNA. The end-point dilution for Factor V mRNA was the same as for U1A mRNA (FIG. 8). Since the sensitivity in NASBA for both analytes is comparable, expression levels of these messages in leukocytes are similar.

Subsequently, nucleic acid extracted from a whole blood sample from a cytomegalovirus-infected patient was analysed for U1A mRNA and IEA mRNA. For this patient, the end-point dilution for U1A mRNA was found to be one 3-fold dilution step less than for the CMV message (data not shown). Therefore, despite the fact that only a subset of the leukocytes is infected by CMV, IEA mRNA still outnumbers U1 mRNA which is anticipated to be expressed in all leukocytes.

CONCLUSION

For a growing number of clinical samples diagnosis at the nucleic acid level is applied. Consequently, quality control of the nucleic acid that is extracted from such a sample becomes an important issue. For clinical samples containing cells, a cellular mRNA can be used to test the extracted material. Succesful amplification of part of such a message, especially when it is expressed at a low level, is indicative both of the amount of nucleic acid that is extracted from a specific sample and of the integrity of the mRNAs in that extract. Here, detection of the human U1A mRNA by NASBA amplification is shown to be a suitable assay to monitor the integrity of RNA extracted from human cells cultured in vitro, from whole blood, or from cervical scrapings. Since this low abundance mRNA is expressed from a housekeeping gene, it can be used for any kind of material containing human cells. Moreover, because of the evolutionary conservation of the U1A protein at the nucleic acid level, the assay might even be applicable to a broader range of vertebrate and even invertebrate species.

REFERENCES

Billings, P. B. and Hoch, S. O. (1984), J. Biol. Chem., 259, 12850–12856.

Boom, R. et al. (1990). Rapid and simple method for purification of nucleic acids. J. Clin. Microbiool. 28, 495–503.

Bringmann, P. et al. (1986) EMBO J., 5, 3509–3516.

Dürst, M., et al. (1983). A papillomavirus DNA from a cervical carcinoma and its prevalence in cancer biopsy samples from different geographic regions. Proc. Natl. Acad. Sci. USA 80, 3812–3815.

Gerna, G., et al. (1991). Monitoring of human cytomegalovirus infections and ganciclovir treatment in heart transplant recipients by determination of viremia, antigenemia, and DNAemia. J. Infect. Dis 164, 488–498.

Green, M. R. (1991). Biochemical mechanisms of constitutive and regulated premRNA splicing. Annu. Rev. Cell Biol. 7, 559–559.

Guthrie, C. (1991). Messenger RNA splicing in yeast: clues to why the spliceosome is a ribonucleoprotein. Science 253, 157–163.

Habets, W. J. et al. (1985a), Clin. Exp. Immunol., 59, 457–466/

Habets, W. J. et al. (1985b) EMBO J., 4, 1545–1550.

Hinterberger, M. et al. (1983), J. Biol. Chem., 258, 2604–2613.

Kinlaw, C. S. et al. (1983), J. Biol. Chem., 258, 7181–7189.

Nelissen, R. L. et al. (1991). Structure, chromosomal localization and evolutionary conservation of the gene encoding human U1 snRNP-specific A protein. Gene. 102, 189–196.

Pettersson, I., et al. (1984), J. Biol. Chem., 259, 5907–5914.

Sillekens , P. T. G. et al. 91987). cDNA cloning of the human U1 snRNA-associated A protein: extensive homoloay between U1 and U2 snRNP-specific proteins. EMBO J. 6, 3841–3848.

Studier, F. W. et al. (1990). Use of T7 RNA polymerase to direct expression of cloned genes. Methods Enzymol. 85, 60–89.

van den Brule et al. (1993). PCR-based detection of genital HPV genotypes: an update and future perspectives. Papillomavirus Rep. 4, 95–99.

Sillekens, P. T. G., Beijer, R. P., Habets W. J. and van Venrooij, W. J. (1988). Human U1 snRNP-specific C protein: complete cDNA and protein sequence and identification of a multigene family in mammals. Nucl. Acids Res. 16, 8307–8321.

---

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO: 1:

```
AATTCTAATA CGACTCACTA TAGGGAGAGG CCCGGCATGT GGTGCATAA          49
```

( 2 ) INFORMATION FOR SEQ ID NO: 2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 2:

```
CAGTATGCCA AGACCGACTC AGA                                     23
```

( 2 ) INFORMATION FOR SEQ ID NO: 3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO: 3:

```
GCATGCCGCC GATGACTCA                                          19
```

( 2 ) INFORMATION FOR SEQ ID NO: 4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO: 4:

```
TGAGTCATCG GCGGCATGC                                          19
```

( 2 ) INFORMATION FOR SEQ ID NO: 5:

( i ) SEQUENCE CHARACTERISTICS:
        ( A ) LENGTH: 22 base pairs
        ( B ) TYPE: nucleic acid

```
( C ) STRANDEDNESS: single
( D ) TOPOLOGY: unknown ( i i ) MOLECULE TYPE: cDNA ( x i ) SEQUENCE DESCRIPTION: SEQ ID NO: 5:

AGAAGAGGAA  GCCCAAGAGC  CA                                                                    2 2
```

I claim:

1. A method for determining the integrity of RNA from a specimen of eukaryotic origin comprising subjecting specimen cDNA to nucleic acid amplification using a first pair of oligonucleotide primers capable of amplifying a specific target nucleic acid sequence to produce a first amplification product and a second pair of oligonucleotide primers capable of amplifying a control nucleic acid encoding a component of a small nuclear ribonucleoprotein (snRNP) particle to produce a second amplification product, and determining whether an amplification product has been produced from the second pair of oligonucleotide primers wherein absence of said second amplification product indicates degradation of the RNA in the specimen.

2. A method according to claim 1, wherein the RNA encodes a component of a small nuclear ribonucleoprotein (snRNP) particle selected from the U1-snRNP specific proteins 70K, C and A.

3. A method according to claim 2, wherein the U1-snRNP specific protein is A.

4. A method according to claim 1, wherein the mRNA is expressed from a single copy gene in a eukaryotic cell.

5. A method according to claim 1, wherein the pair of oligonucleotide primers is selected such that the amplified sequence comprises at least one exon-exon junction.

6. A method according to claim 1, wherein the pair of oligonucleotide primers is selected such that the amplification product comprises at least a part of a nucleic acid sequence which is either identical to or complementary to exon 4 of the nucleic acid sequence encoding U1-snRNP protein A.

7. A method according to claim 6, wherein the pair of oligonucleotide primers is selected such that the amplification product comprises at least the exon (n−1)-exon (n) junction, wherein n is an integer indicative of the exon number.

8. A method according to claim 1, wherein the pair of oligonucleotide primers is selected such that the amplification product comprises at least the exon (n)-exon (n+1) junction, wherein n is an integer indicative of the exon number.

9. A method according to claim 6, wherein the oligonucleotide primer pair comprises
a primer which is either identical to or complementary to a part of exon (n−1) of the nucleic acid sequence encoding U1-snRNP A and
a primer which is either identical to or complementary to part of the nucleic acid sequence of exon (n) of the nucleic acid sequence encoding U1-snRNP A and/or which is either identical to or complementary to part of the nucleic acid sequence downstream of exon (n) of the nucleic acid sequence encoding snRNP A.

10. The method of claim 1, wherein said RNA is mRNA and the eukaryotic species is human.

11. The method of claim 1, wherein the product of the amplification is quantified.

12. The method of claim 2, wherein said RNA encodes a component of a major snRNP particle.

13. The method of claim 12, wherein said major snRNP particle is U1-snRNP.

* * * * *